United States Patent [19]

Creager

[11] Patent Number: 5,319,982
[45] Date of Patent: Jun. 14, 1994

[54] DEVICE FOR MONITORING THE FATIGUE LIFE OF A STRUCTURAL MEMBER AND A METHOD OF MAKING SAME

[75] Inventor: Matthew Creager, West Hills, Calif.

[73] Assignee: Tensiodyne Scientific, Inc., West Los Angeles, Calif.

[21] Appl. No.: 907,364

[22] Filed: Jul. 1, 1992

[51] Int. Cl.⁵ ............................................. G01N 19/08
[52] U.S. Cl. ...................................... 73/762; 73/799; 73/787
[58] Field of Search .................. 73/762, 808, 809, 810, 73/786, 787, 799, 806, 775

[56] References Cited

U.S. PATENT DOCUMENTS

| | | | |
|---|---|---|---|
| 4,164,874 | 8/1979 | Cassat et al. | 73/799 |
| 4,590,804 | 5/1986 | Brull | 73/762 |

FOREIGN PATENT DOCUMENTS

| | | | |
|---|---|---|---|
| 938093 | 6/1982 | U.S.S.R. | 73/799 |
| 1504548 | 8/1989 | U.S.S.R. | 73/809 |

*Primary Examiner*—Hezron E. Williams
*Assistant Examiner*—Nashmiya Ashraf
*Attorney, Agent, or Firm*—Sprung Horn Kramer & Woods

[57] ABSTRACT

A device for monitoring the fatigue life of a structural member composed of a predetermined material, and a method of making same. The device is a substantially flat fuse composed of a material similar to the predetermined material and mountable on a structural member during use. The fuse has cut out portions which define fuse elements which also have reduced thicknesses to effect failure at different times in sequence because of fatigue and prior to the failure of the monitored structural member when the fuse and the monitored structural member are subjected to substantially the same stress history.

13 Claims, 3 Drawing Sheets

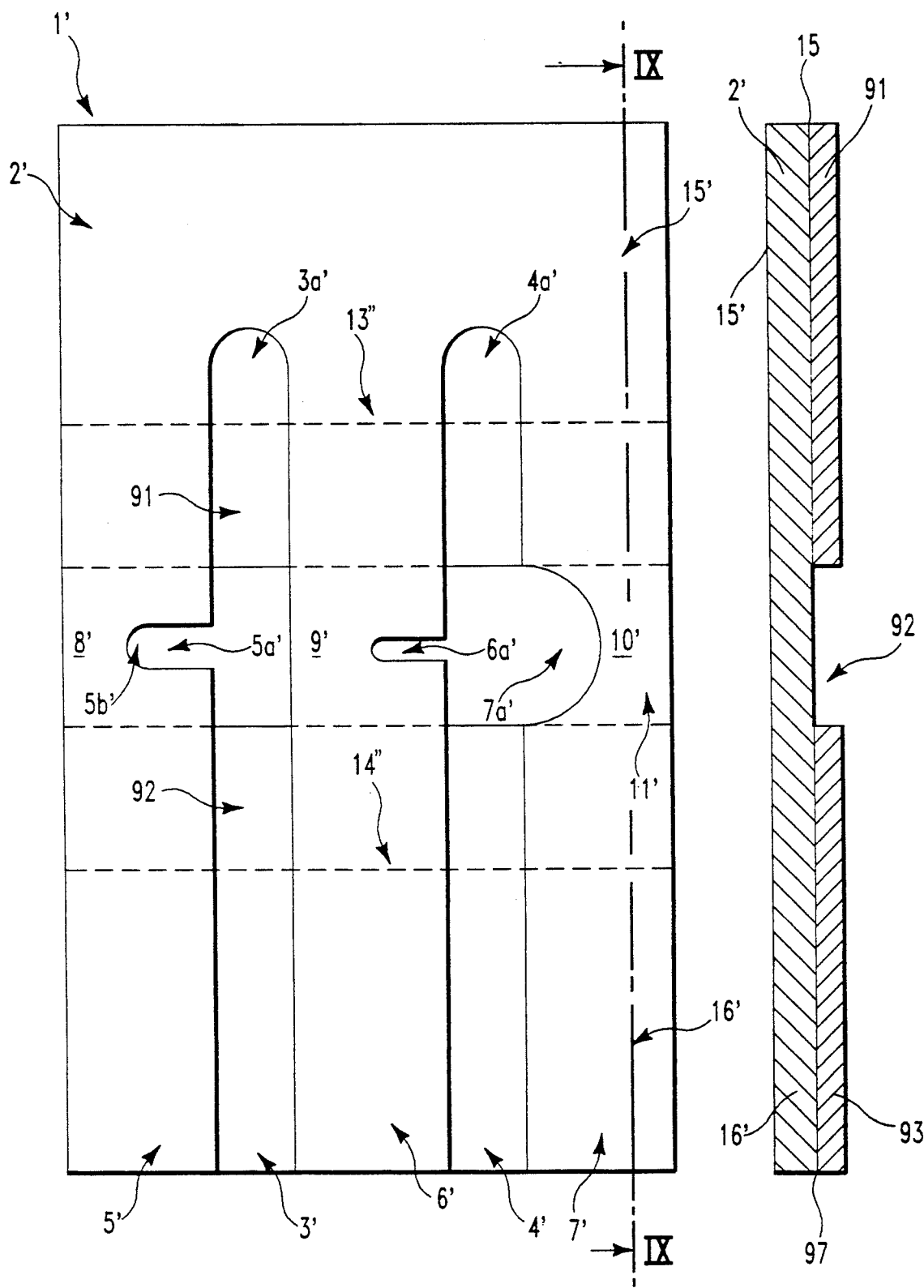

DEVICE FOR MONITORING THE FATIGUE LIFE OF A STRUCTURAL MEMBER AND A METHOD OF MAKING SAME

BACKGROUND OF THE INVENTION

1. Field of the Invention

This invention relates to fatigue monitors and more particularly to a novel and highly effective device for detecting fatigue of a monitored structure due to flexure and to a method of making the device. The invention is applicable particularly to the detection of metal fatigue but is applicable also to the detection of fatigue in other structural materials.

2. Description of the Prior Art

Maurice A. Brull U.S. Pat. Nos. 4,590,804 and 4,639,997, both assigned to the assignee of the present invention, disclose respectively a device for and method of monitoring fatigue life. The patents illustrate what are called coupons, otherwise known as fatigue fuses, arranged in a row and each having different notch patterns ranging from the mildest notch pattern to the most aggressive notch pattern. The coupons will fail because of fatigue in a prescribed sequence. The number of load cycles to failure as a function of stress amplitude for the different coupons can be plotted, and as each coupon fails, it gives an indication of the remaining life expectancy of the monitored structure.

More particularly, each of the coupons includes a special notch pattern. The coupon axis must be oriented along a suitably chosen direction. The notch pattern of each of the coupons produces a stress field which varies in intensity from relatively mild to very severe. The severity of the local stress field is controlled by the geometry of the notch pattern. Smooth geometries produce a mild stress concentration, while geometric discontinuities produce severe stresses. In this manner, when all of the coupons are subjected to the same stress history, it will result in the development of different stress concentrations in the region of the notch tips of each coupon, so that each coupon will have a different fatigue life. Moreover, if the stress history of the coupons is the same as that of the monitored structure, the fatigue life of each coupon will be a different percentage of the fatigue life of the monitored structure.

In accordance with the disclosures of the patents, the coupons are secured to the monitored structure by pins, adhesive or welding so that, ideally, all of the coupons experience the same strain history as the monitored structure.

SUMMARY OF THE INVENTION

An object of the present invention is to obtain an improvement over the device disclosed in the prior art.

Another object of the present invention is to provide a device for monitoring the fatigue life of a structural member by utilizing a fatigue fuse which can be controlled via geometry to more sensitively detect failure at a range of percentages of the fatigue life of the monitored structural member.

A still further object of the present invention is to provide a method of making the above-mentioned devices.

These and other objects of the present invention are achieved in accordance with the present invention by a device for monitoring the fatigue life of a structural member composed of a predetermined material, wherein the device is a substantially flat fuse composed of the predetermined or similar material and mountable on the structure during use. The fuse cut out portions define fuse elements. The defined fuse elements have different shapes configured to fail at different times in sequence because of fatigue and prior to the failure of the monitored structural member when the fuse and the monitored structural member are subjected to substantially the same stress history.

In accordance with the invention, a cut out portion is formed on at least one side of each fuse leg, each cut out portion having a different configuration.

The fuse is made more sensitive by a modification that focusses strain (and stress) into the notch area. This can be done in the following ways: thinning the fuse leg along the central portion of the unbonded region, thickening the fuse leg external to the central portion of the unbonded region, or attaching a stiffer material to the fuse leg in the region external to the unbonded region.

In a preferred embodiment of the invention, the fuse elements have a reduced thickness as compared with the remainder of the fuse in order to control the percentage of the fatigue life that the fuse elements will fail at. The reduced thickness is in the form of a channel which has a constant depth or a variable depth.

In accordance with another independent aspect of the present invention, a method of making a device for monitoring the fatigue life of a structural member comprises obtaining a thin sheet of material from which the structural member is fabricated and cutting out portions to define the fuse members.

The device for monitoring the fatigue life according to the present invention comprises a substantially flat fuse having means forming at least one fuse leg, a cut out portion on at least one side of the leg to define a fuse element, and means effecting a reduced thickness of the fuse element relative to the remainder of the fuse. The device can have a plurality of legs where the cut out portions of the legs have different shapes and the reduced thickness of the fuse element is the same. This effects failure of the fuse elements at different percentages of the fatigue life of the structural member to which the device is attached. The fuse elements can have different reduced thicknesses relative to the remainder of the fuse to effect failure of the fuse elements at different percentages of the fatigue life of the structural member and the cut out portions can have the same shape in this instance.

The means for effecting a reduced thickness can comprise a channel in one or both faces of the fuse or it can be formed by bonding flat members on one face of the fuse on both sides of the fuse elements. The flat members can be composed of the same material as the fuse or of a stiffer material than the fuse.

The reduced thickness area can vary from leg to leg and is in the range of 10 to 90% of the remaining thickness of the fuse.

These and other features and advantages of the present invention will be understood from the following detailed description from the present invention and the accompanying drawing, wherein:

BRIEF DESCRIPTION OF THE DRAWINGS

FIG. 8 is a plan view of a further embodiment of the device according to the present invention, and FIG. 9 is a sectional view of FIG. 8 along line IX—IX.

DETAILED DESCRIPTION OF THE INVENTION

Figures 1, 2:
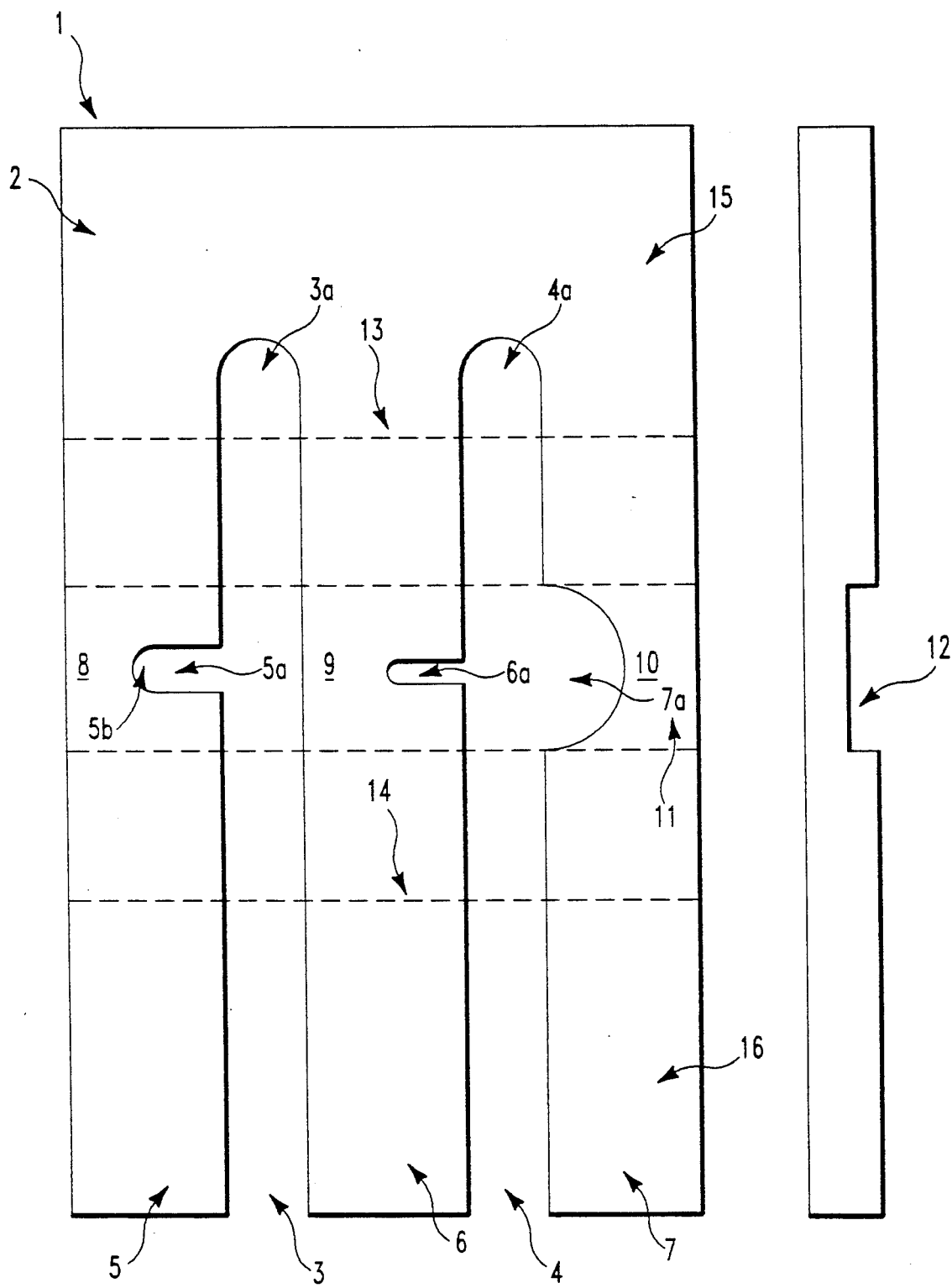
FIG. 1 is a plan view of a device for monitoring the fatigue life of a structural member in accordance with the present invention.
FIG. 2 is a side view of FIG. 1.

FIG. 1 shows a device for detecting fatigue of a monitored structure due to flexure, the monitored structure being made of a predetermined material. While the monitored structure is not illustrated, it can be a part of a bridge, ship, bulldozer, truck, mobile missile, gun mount, commercial electric power generator (nuclear or conventional), chemical plant, tower, crane, oil rig, airplane, etc. In an airplane, to take just one example, the part monitored can be an inboard or outboard stringer splice, a floor system, a wing-fuselage tee, a spar cap splice, etc. In general, the part monitored can be flat, concave or convex. Typically, the predetermined material of which the monitored structure is made will be an aluminum alloy or a steel alloy, although it may be another metal, a plastic, or any other structural material subject to failure because of fatigue. The monitored structure and the fuse may be made, for example, of 7075 aluminum, 6061 aluminum, 2024 aluminum, 1018 mild steel, 316 stainless steel, titanium, etc.

The device shown in FIG. 1 comprises a fuse 1 made of the same or similar material as the structural member to be monitored and is formed from a thin integral blank of sheet material 2. The blank 2 has first and second elongated slots 3, 4 forming three fuse legs 5, 6, 7. Fuse leg 5 has cut out portion 5a, fuse leg 6 has cut out portion 6a and fuse leg 7 has cut out portion 7a to form fuse elements 8, 9 and 10 respectively.

As shown, cut out portion 5a and cut out portion 6a are elongated and cut out portion 7a is a section of a circle.

The three fuse elements 5, 6, 7 which are thus formed, have a different configuration, calculated to fail at different times in sequence because of fatigue and prior to the failure of the monitored structural member when the fuse and the monitored structural member are subjected to substantially the same stress history.

The percentage of fatigue which defines the time that each fuse member will fail is also determined by the reduced thickness or scarf out zone 11 which includes a channel 12 formed at one or both faces of the fuse.

The fuse is attached to the structural member by adhesive bonding. The adhesive acts as an insulator which insulates the fuse from the structural member. In this way the fuse legs can be remotely monitored by electrical means to determine if the fuse element corresponding thereto has failed. The method and apparatus for carrying this out is disclosed in copending U.S. application Ser. No. 07/677,163 filed Mar. 29, 1991 now U.S. Pat. No. 5,237,875, and assigned to the same assignee. The disclosure of that application is incorporated by reference herein.

The operation of the fuse is also controlled by the extent to which it is bonded to the structural member. As shown, two bonding lines 13, 14 are indicated to demarcate the areas 15 and 16 of the fuse which receive adhesive and are bonded to the structural member during use.

EXAMPLE 1

The fuse 1 is composed of an aluminum Al 7075 T6 alloy and has a length of 2" and a width of 0.8750" and a thickness of 0.04 inches. The radius of cut out portion 7a is 0.0625". The length of cut out 6a is 0.0625" and the width is 0.002". The length of cut out 5a is 0.0625" and the width is 0.025". The radius of the circular portion 5b at the end thereof is 0.0125". The line of symmetry of the cut out portions 5a–7a is midway along the length of the fuse. The slots 3 and 4 are identical and spaced 0.25" from the edges. They have a length of 1.25" and a width of 0.0625", with the radius of the circular portions 3a, 4a at the end being 0.03125". The channel 12 has a width of 0.075" and a depth of 0.012". The bonding lines 13, 14 are 0.85" from the ends of the fuse.

The fuse elements 9, 8 and 10 fail in sequence at different percentages of the fatigue life of the aluminum alloy.

The fuse 1 as shown in FIG. 1 is formed by obtaining a thin sheet of material 2 from which the structural member to be monitored is fabricated and cutting out portions 3, 4 and 5a–7a from the sheet of material by punching on a press or by wire cutting electro-discharge machinery. The channel is formed by milling on a milling machine.

FIGS. 3–7 show another embodiment of the present invention including a fuse 31 made of the same material as the structural member to be monitored and is formed from a thin integral blank of sheet material 32. The blank has three elongated slots 33, 34, 35 forming four fuse legs 36, 37, 38 and 39. Fuse legs 36–39 have cut out portions 36a–39a to form fuse elements 45–48 respectively.

Figure 3:
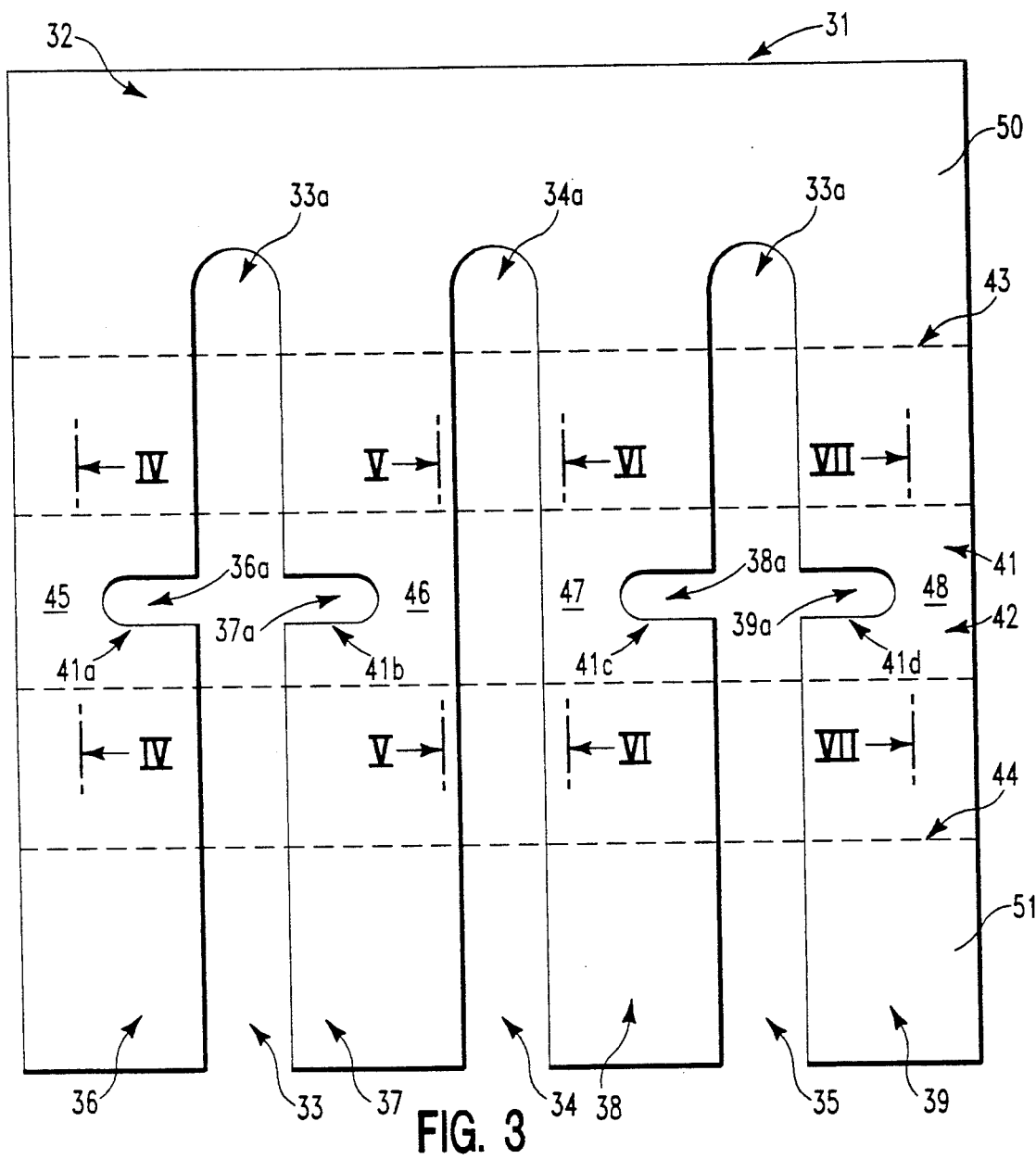
FIG. 3 is a plan view of another embodiment of the device according to the present invention.
Figure 4:
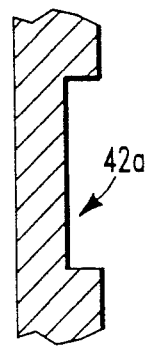
FIG. 4 is a partial sectional view along line IV—IV in FIG. 3.
Figure 5:
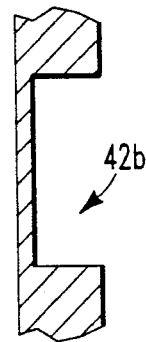
FIG. 5 is a partial sectional view along line V—V in FIG. 3.
Figure 6:
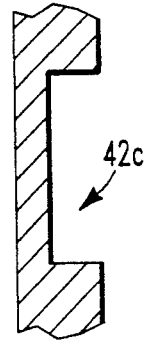
FIG. 6 is a partial sectional view along line VI—VI in FIG. 3.
Figure 7:
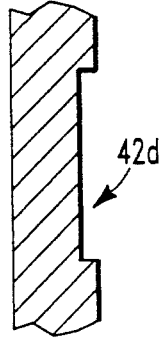
FIG. 7 is a partial sectional view along line VII—VII in FIG. 3.

As shown in FIG. 3, cut out portions 36a–39a are elongated terminating in a semicircular edge.

The four fuse elements 45–48 which are thus formed have the same configuration. The fuse elements are configured to fail at different times in sequence as a result of the variable reduced thickness or scarf out zone 41 formed at the underside thereof. The reduced thickness zone 41 includes four separate sections 41a–41d. As shown in FIGS. 4–7, the reduced thickness is achieved by the formation of a channel 42 which has four discrete steps therein. Each of the channel portions 42a–42d has a different depth, and as a result, each fuse member will fail at a different time determined by the depth of the channel.

It should be clear that the fuse will also operate when both the thickness varies and the shape of the cut outs are different. The reduced thickness can vary from 10 to 90% of the overall thickness of the fuse. The channels can be formed on one or both surfaces of the fuse.

The embodiment shown in FIG. 3 is also bonded to a structural member during use. For this purpose, bonding lines 43, 44 are shown to demarcate the areas 50, 51 in which adhesive is applied for bonding the fuse to the structural member during use.

EXAMPLE 2

The fuse 31 is composed of an Al 7075 T6 alloy and has a length of 2" and a width of 1.1875" and a thickness of 0.04". Each slot 33-39 is identical and has a length of 1.25" with the internal end terminating in a circular area having a radius of 0.03125". The width of each slot 33-35 is 0.0625" and each leg 36-39 has a width of 0.25".

The cut outs 36a-39a are identical and have a length of 0.0625" and with a radius at the internal end of 0.0125". Each cut out portion 36a-39a has a width of 0.025".

The bonding lines 43 and 44 are 0.85" from the edges of the fuse.

All of the cut outs and the channel 42 are disposed symmetrically about a center line of the fuse 31. The channel has a width of 0.075" and channel section 42a has a depth of 0.018", channel portion 42b has a depth of 0.008", channel portion 42c has a depth of 0.012" and channel portion 42d has a depth of 0.03".

As a result of this configuration, fuse elements 46, 47, 45 and 48 fail in sequence at different percentages of the fatigue life of the aluminum alloy.

Fuse 31, as shown in FIG. 3, is formed by obtaining a thin sheet of material from which the structural member to be monitored is fabricated and cutting out portions 33-39 and 36a-39a from sheet of material by punching on a press or by wire cutting electro-discharge machinery. The variable channel is formed by milling each section to a different depth on a milling machine.

FIGS. 8 and 9 show another embodiment of the present invention. In this embodiment, all of the elements shown in FIGS. 8 and 9 which are similar in structure and function to those of FIGS. 1 and 2 are labeled with a "prime".

In the present invention, the reduced thickness zone 11' is not a channel as in the embodiment of FIGS. 1 and 2, but rather is formed by bonding flat members 91 and 93 with adhesive layers 95 and 97, respectively, on the fuse 2'. As a result of the configuration of flat members 91 and 93, the space 92 is left which has a reduced thickness from that of the remaining areas of the fuse 2'. The area 92 includes the fuse members 8'-10' because flat members 91 and 93 are on both sides of the fuse elements.

The fuse shown in FIGS. 8 and 9 is bonded to a structural member at sponding areas 15' and 16'. The flat members 91 and 93 can be composed of the same material as the fuse 2' or can be made from a stiffer material. Thus, if the fuse 2' is made from an aluminum, the flat members 91 and 93 can be made from steel or a composite material such as graphite epoxy.

Many modifications of the preferred embodiments of the invention described above will readily occur to those skilled in the art upon consideration of this disclosure. For example, the configuration of the notches can be changed as well as the dimensions of the fuse member and the fuse elements thus formed. The number of fuse elements can be increased or decreased. Accordingly, the invention is not limited except as to the following claims.

What is claimed is:

1. A device for monitoring the fatigue life of a structural member composed of a predetermined material, the device comprising: a substantially flat fuse composed of a material of similar composition to said predetermined material mountable on the structural member, said fuse having means defining at least two fuse legs, each leg having a cut out portion on at least one side thereof to delimit a fuse element therein and means forming a reduced thickness of each fuse element relative to a remainder of the fuse and wherein the fuse elements each have a different reduced thickness, whereby a configuration of the cut out portion and reduced thicknesses effect a failure of the fuse elements at different percentages of fatigue life of the structural member due to fatigue prior to a failure of the structural member when the fuse and the structural member are subjected to a substantially similar stress history.

2. The device according to claim 1, wherein the means defining at least two fuse legs comprises at least one elongated slot.

3. The device according to claim 2, wherein the cut out portions of the legs have different shapes.

4. The device according to claim 1, wherein the fuse and the structural member are composed of the same material.

5. The device according to claim 1, wherein the cut out portions have the same shape.

6. The device according to claim 1, wherein the fuse and the structural member are composed of a metal.

7. The device according to claim 1, wherein the means forming reduced thicknesses comprises channels in the fuse legs.

8. The device according to claim 7, wherein the channel is in one surface of the fuse.

9. A method of making a device for monitoring the fatigue life of a structural member composed of a predetermined material, the method comprising the steps of: providing a substantially flat blank fuse composed of a material of similar composition to said predetermined material, defining at least two fuse legs by cutting an elongated slot in the fuse, forming at least two fuse elements in the fuse by cutting out portions thereof and reducing the thickness of each of the fuse elements relative to the remainder of the fuse, wherein the fuse elements each have a different reduced thickness to effect a failure of the fuse elements at different percentages of fatigue life of the structural member and prior to a failure of the structural member when the fuse elements and the structural member are subjected to a substantially similar stress history.

10. The method according to claim 9, wherein the step of reducing comprises reducing the thickness of each fuse element by a different amount in the range of 10 to 90%.

11. The method according to claim 9, wherein the step of reducing the thickness comprises forming a channel in the fuse.

12. The method according to claim 11, wherein the channel is formed in one surface of the fuse.

13. The method according to claim 9, wherein the step of reducing comprises bonding two flat members to one surface of the fuse on opposite sides of each fuse element.

* * * * *